United States Patent
Anderson (10) Patent No.: US 9,062,771 B2
(45) Date of Patent: Jun. 23, 2015

(54) METHODS AND APPARATUS FOR ESTIMATING USEFUL LIFE OF A SEAL

(75) Inventor: Shawn William Anderson, Haverhill, IA (US)

(73) Assignee: FISHER CONTROLS INTERNATIONAL LLC, Marshalltown, IA (US)

( * ) Notice: Subject to any disclaimer, the term of this patent is extended or adjusted under 35 U.S.C. 154(b) by 726 days.

(21) Appl. No.: 13/371,263

(22) Filed: Feb. 10, 2012

(65) Prior Publication Data

US 2013/0211735 A1    Aug. 15, 2013

(51) Int. Cl.
*F16K 37/00* (2006.01)
*F16J 15/06* (2006.01)
*G01M 13/00* (2006.01)
*G05B 23/02* (2006.01)
*F16K 41/10* (2006.01)

(52) U.S. Cl.
CPC ............ *F16J 15/064* (2013.01); *G01M 13/005* (2013.01); *G05B 23/0283* (2013.01); *F16K 41/10* (2013.01); *F16K 37/0083* (2013.01)

(58) Field of Classification Search
CPC ......................... F16K 37/0075; F16K 37/0083
USPC .......................................................... 702/34
See application file for complete search history.

(56) References Cited

U.S. PATENT DOCUMENTS

2008/0252475 A1* 10/2008 Jensen et al. .................. 340/683

FOREIGN PATENT DOCUMENTS

EP         2075663 A1       7/2009

OTHER PUBLICATIONS

Patent Cooperation Treaty, "International Search Report," issued in connection with Application No. PCT/US2013/025486, Jun. 26, 2013, 2 pages.
Patent Cooperation Treaty, "Written Opinion of the International Searching Authority," issued in connection with Application No. PCT/US2013/025486, Jun. 26, 2013, 3 pages.

* cited by examiner

*Primary Examiner* — Bryan Bui
(74) *Attorney, Agent, or Firm* — Hanley, Flight & Zimmerman, LLC (57) ABSTRACT

Methods and apparatus for estimating useful life of a seal in a process control device are disclosed. An example method includes establishing a plurality of travel ranges of a stem or shaft of a process control device. Each travel range corresponds to different values corresponding to stresses experienced by the seal of the process control device during an operational cycle. The example further includes determining a count of operational cycles associated with each of the travel ranges and estimating a total amount of useful life of the seal consumed based on the counts.

20 Claims, 7 Drawing Sheets

TABLE 1. ESTIMATED LIFE CYCLE FOR BELLOWS AT 150 Psig AND 100°F

| VALVE SIZE, NPS | | BELLOWS SEAL TRAVEL | | | | | | | | | | | | | | |
|---|---|---|---|---|---|---|---|---|---|---|---|---|---|---|---|---|
| | | mm | inch | mm | inch | mm | inch | mm | inch | mm | inch | mm | inch | mm | inch |
| 1/2, 3/4, 1, & 1-1/2 | 1 Ply | 3.6 | 0.14 | 4.8 | 0.19 | 7.1 | 0.28 | 9.7 | 0.38 | 14.2 | 0.56 | 19.1 | 0.75 |
| | 2 Ply | 10,000,000 | | 8,000,000 | | 1,400,000 | | 550,000 | | 150,000 | | 50,000 | |
| 2 | 1 Ply | 5.3 | 0.21 | 7.1 | 0.28 | 10.7 | 0.42 | 14.2 | 0.56 | 22.3 | 0.88 | 28.6 | 1.12 |
| | 2 Ply | 10,000,000 | | 4,000,000 | | 2,500,000 | | 800,000 | | 150,000 | | 50,000 | |
| 3 | 1 Ply | 8.4 | 0.33 | 9.5 | 0.38 | 14.2 | 0.56 | 19.1 | 0.75 | 28.6 | 1.12 | 38.1 | 1.50 |
| | 2 Ply | 1,000,000 | | 700,000 | | 450,000 | | 300,000 | | 100,000 | | 50,000 | |
| 4 | 1 Ply | 9.5 | 0.38 | 12.7 | 0.5 | 19.1 | 0.75 | 28.6 | 1.12 | 38.1 | 1.50 | 50.8 | 2.00 |
| | 2 Ply | 10,000,000 | | 5,000,000 | | 2,500,000 | | 1,000,000 | | 350,000 | | 150,000 | |

METHODS AND APPARATUS FOR ESTIMATING USEFUL LIFE OF A SEAL

FIELD OF THE DISCLOSURE

This disclosure relates generally to seals and, more particularly, to methods and apparatus for estimating useful life of a seal.

BACKGROUND

Process control systems generally use a variety of process control devices to control a process. The process control devices often include seals (e.g., bellows seals) that are subjected to stresses while the process is controlled. Over time, the stresses may cause the seals to fail. Many factors may affect useful life of a seal such as stress amplitudes, geometry of the seal, environmental conditions (e.g., temperatures, pressures, corrosion, etc.), and/or other factors. During operation, these factors often vary, and, as a result, the useful life of a seal may vary. A seal may be periodically visually inspected and/or replaced to prevent an unexpected failure of the seal. Nevertheless, seals often fail before the seals are replaced, or the seals are replaced substantially before the useful lives of the seals are consumed.

SUMMARY

An example method of estimating useful life of a seal in a process control device includes determining a plurality of operational cycles of a stem or shaft of the process control device and determining a value corresponding to a stress experienced by the seal for each of the operational cycles. The example method further includes estimating a total amount of useful life of the seal consumed based on each of the values.

Another example method of estimating useful life of a seal in a process control device includes establishing a plurality of travel ranges of a stem or shaft of the process control device. Each travel range corresponds to different stresses experienced by the seal during an operational cycle. The example method further includes determining a count of operational cycles associated with each of the travel ranges and estimating a total amount of useful life of the seal consumed based on the counts.

DETAILED DESCRIPTION

While the following example apparatus and methods are described in conjunction with bellows seals, the example apparatus and methods may also be used with any other seal to be subjected to stress. In industrial processes (e.g., oil and gas distribution systems, chemical processing plants, etc.), the processes are often controlled by a variety of process control devices such as linear valves. Generally, the process control devices include seals to prevent fluid leakage. For example, a linear valve often includes a plug coupled to a sliding stem to control fluid flow and a bellows seal to prevent fluid leakage. During operation, the stem moves and typically subjects the seal to loads and, thus, stresses. Generally, the stresses cause structural damage (e.g., microscopic cracks) to the seal and, over time, may result in fatigue and sudden failure of the seal. A useful life of the seal may be affected by a variety of factors such as, for example, stress amplitudes, number of loads, geometry of the seal, material type of the seal, internal defects of the seal, environmental conditions (e.g., pressures, temperatures, corrosion, erosion, etc.), and/or other factors. During operation, stem travel distances, stem positions, environmental conditions, and/or other conditions may vary while the process is controlled.

The example apparatus and methods disclosed herein may be used to estimate useful life of a seal in a process control device. An example method disclosed herein includes determining a plurality of operational cycles of a stem or shaft of the process control device and determining a value corresponding to a stress experienced by the seal for each operational cycle. The example method further includes estimating a total amount of useful life of the seal consumed based on each of the values. In some examples, based on the estimated total amount of useful life of the seal consumed, the remaining useful life of the seal is estimated.

Estimating the total amount of useful life of the seal may include establishing a plurality of travel ranges of the stem or shaft of the process control device. Each travel range may correspond to different values corresponding to stresses experienced by the seal. Each of the values may be associated with only one of the travel ranges, and a count of values associated with each of the travel ranges may be determined. A ratio for each count and associated travel range may be calculated. In some examples, the ratios are calculated by dividing each count by a predetermined estimated cycle life value corresponding to the travel range associated with the count. The ratios may then be summed to determine a value indicative of the total amount of useful life of the seal consumed.

Figure 1:
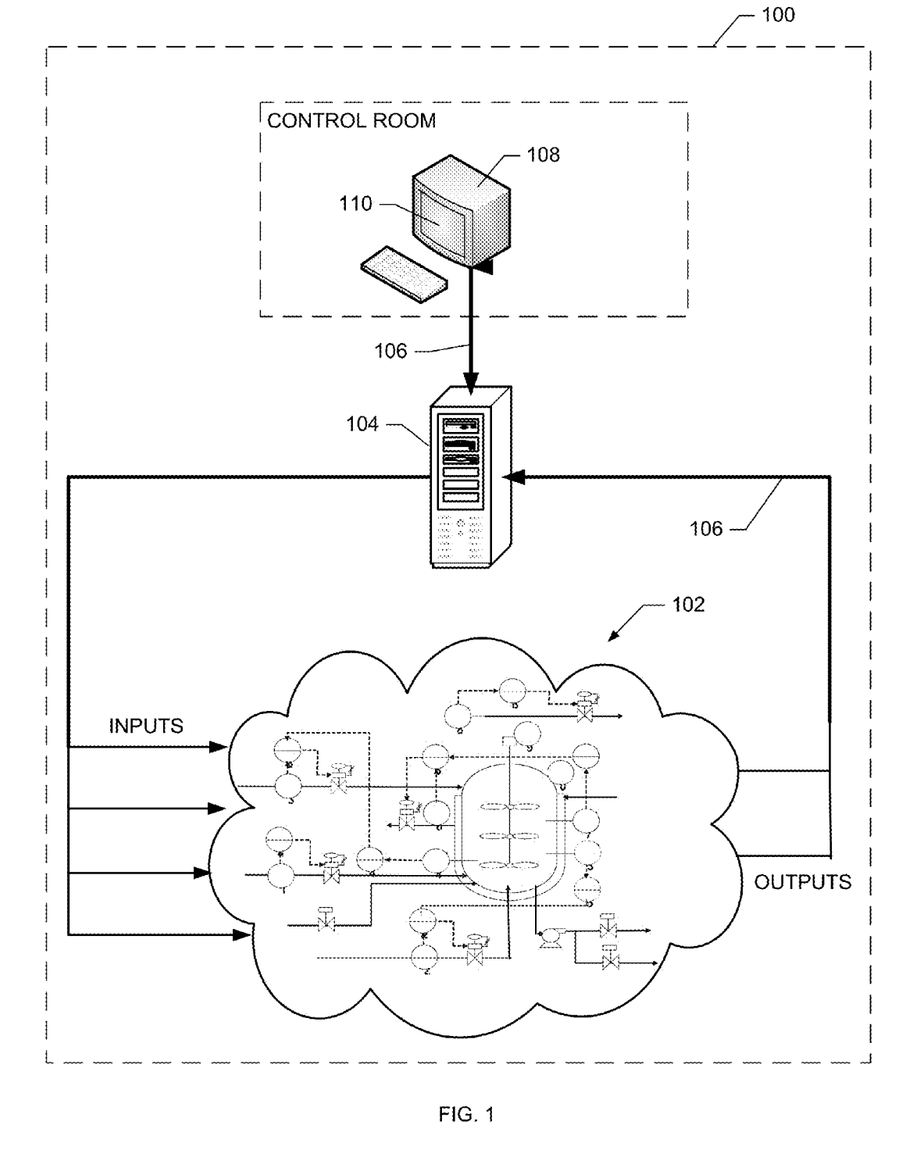
FIG. 1 illustrates an example process control system within which the teachings of this disclosure may be implemented.

FIG. 1 illustrates an example process control system 100 that may be used to implement the example apparatus and methods disclosed herein. The example process control system 100 includes any number of process control devices 102 such as input devices and/or output devices. In some examples, the input devices include valves, pumps, fans, heaters, coolers, mixers, and/or other devices, and the output devices include thermometers, pressure gauges, concentration gauges, fluid level meters, flow meters, vapor sensors, valve positioners, and/or other devices. The input and output devices are communicatively coupled to a controller 104 (e.g., a DeltaV™ controller) via a data bus (e.g., Profibus™) or local area network (LAN) 106. The controller 104 transmits instructions to the input devices to control the process and receives and/or collects information (e.g., measured process information, environmental information, and/or input device information, etc.) transmitted by the output devices. The controller 104 generates notifications, alert messages, and/or other information, and the input and output devices may be wirelessly communicatively coupled to the controller 104. The controller 104 is also communicatively coupled to a workstation 108, which includes an interface 110 that displays process control information (e.g., measured process control information, alert message, etc.). Although a single controller 104 is shown in FIG. 1, one or more additional controllers may be included in the example system 100 without departing from the teachings of this disclosure.

Figure 2A:
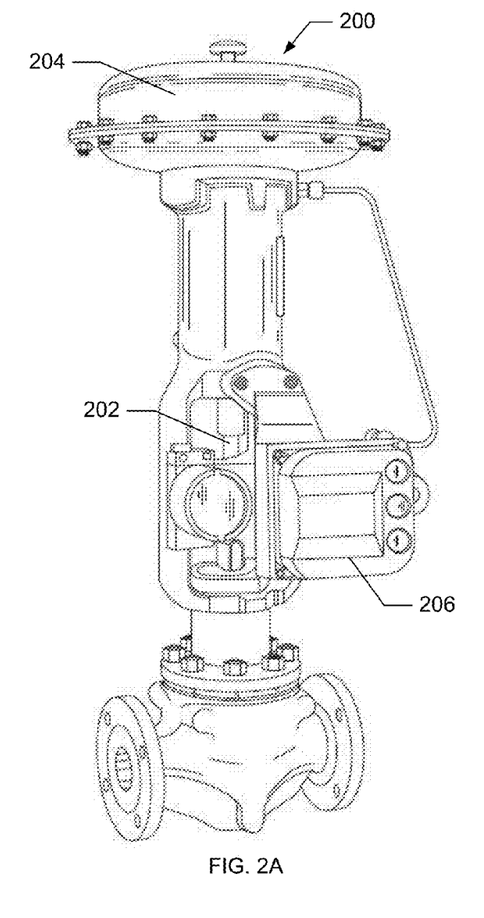
FIG. 2A depicts an example process control device that may be used to implement example methods disclosed herein.
Figure 2B:
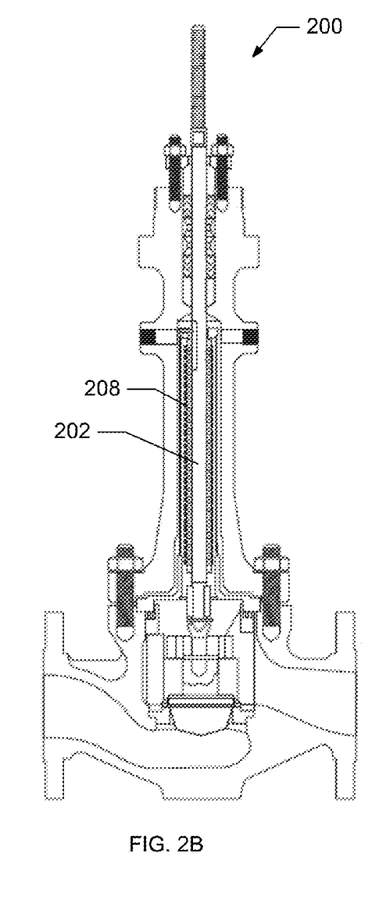
FIG. 2B is a cross-sectional view of the example process control device of FIG. 2A.

FIGS. 2A and 2B depict an example process control device 200 that may be used to implement the example methods disclosed herein. The example process control device 200 depicted in FIGS. 2A and 2B is a linear valve. Other process control devices having a seal subjected to stress during operation (e.g., a rotary valve including a shaft) may also be used to implement the example methods disclosed herein. The example process control device 200 includes a sliding stem 202 and an actuator 204 to move the sliding stem 202. The example process control device 200 also includes a digital valve positioner 206 ("DVP") (e.g., Fisher® FIELDVUE™ DVC6200p Digital Valve Controller) to collect and determine information such as, for example, a position of the stem 202, a direction of stem travel, a count of operational cycles, and/or other information. During operation, the DVP 206 transmits the information to the controller 104 and receives instructions from the controller 104.

FIG. 2B is a partial, cross-sectional view of a portion of the process control device 200 of FIG. 2A. The process control device 200 includes a bellows seal 208 to provide a fluid seal. During operation, the process control device 200 performs a plurality of operational cycles. In some example operational cycles, the actuator 204 moves the stem 202 from a first position to a second position in a first direction (e.g., upward in the orientation of FIGS. 2A and 2B), and the DVP 206 determines an operational cycle and a value corresponding to a stress experienced by the seal 208 for the operational cycle.

For example, when the stem 202 is the first position, the DVP 206 determines the position of the stem 202. As the stem 202 moves from the first position in the first direction, the DVP 206 determines a beginning of the operational cycle. When the stem 202 reaches the second position, the DVP 206 again determines the position of the stem 202. When the stem 202 moves from the second position in a second direction opposite the first direction, the DVP 206 determines an end of the operational cycle and a beginning of another operational cycle at the second position.

The DVP 206 then determines the value corresponding to the stress experienced by the seal 208 for the operational cycle. In some examples, the value corresponding to the stress experienced by the seal 208 for the operational cycle is a distance traveled by the stem 202 during the operational cycle. The DVP 206 determines the distance traveled by the stem 202 during the operational cycle by determining a distance between the first position and the second position.

In other examples, the value corresponding to the stress experienced by the seal 208 for the operational cycle is a position of the stem 202 during the operational cycle farthest from a position of the stem 202 where the seal 208 experiences about zero stress. In such examples, the DVP 206 determines the position of the stem 202 farthest from the position of the stem 202 where the seal 208 experiences about zero stress by determining whether the first position is farther than the second position from the position of the stem 202 where the seal 208 experiences about zero stress. In the illustrated example, the position of the stem 202 where the seal 208 experiences about zero stress is a fully closed position (e.g., 0 inches). The second position (e.g., 0.25 inches) is farther than the first position (e.g., 0.1 inches) from the fully closed position and, thus, the second position is the value corresponding to the stress experienced by the seal for the operational cycle.

During each operational cycle, the bellows seal 208 is subjected to a load and, thus, a stress. As a result, a portion of useful life of the seal 208 is consumed during each operational cycle. An amount of the useful life consumed during one of the operational cycles is affected by a distance traveled by the stem 202 during the operational cycle; a position of the stem 202 during the operational cycle relative to the position of the stem 202 where the seal 208 experiences about zero stress; a diameter of the stem 202; process conditions such as temperature and pressure; and/or other factors.

Figure 3:
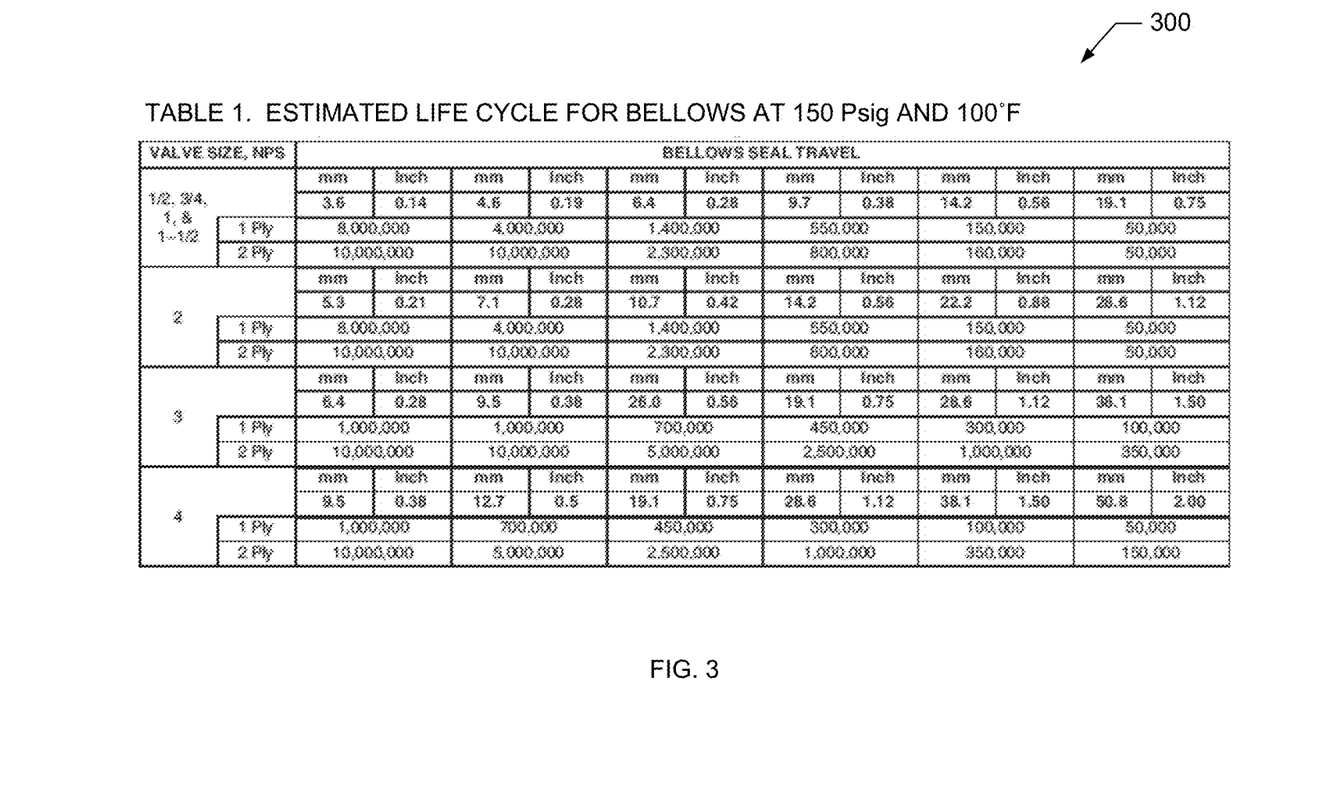
FIG. 3 is a table illustrating example predetermined estimated cycle life values that may be used to implement the example methods disclosed herein.

FIG. 3 is a table 300 illustrating example predetermined estimated cycle life values for bellows seals. The example predetermined estimated cycle life values are determined by testing a plurality of other process control devices similar or identical to a process control device of the example process control system 100. During each test, a stem of one of the similar or identical process control devices travels a predetermined distance for each operational cycle until a seal of the process control device fails. The stem travels to and from a position where the seal experiences about zero stress to a second position the predetermined distance away from the position of the stem where the seal experiences about zero stress. A temperature and/or a pressure (e.g., 100° F. and 150 Psig) may remain substantially constant throughout each test. For example, the stem of one of the similar or identical process control devices travels 0.21 inches for each operational cycle, and after 8,000,000 operational cycles, the seal of the process control device fails. Thus, a predetermined estimated cycle life value is 8,000,000 operational cycles. Other similar or identical process control devices are tested to determine a plurality of predetermined estimated cycle life values. Based on a plot (not shown) of the experimentally determined estimated cycle life values, known curve fitting techniques may be used to determine other predetermined estimated cycle life values. As discussed in greater detail below, the predetermined estimated cycle life values are used to estimate a useful life of the seal 208 in the process control device 200 in the process control system 100.

FIGS. 4, 5, 6, and 7 are flowcharts representative of example methods disclosed herein. Some or all of the example methods of FIGS. 4, 5, 6, and 7 may be carried out by a processor, the controller 104 and/or any other suitable processing device. In some examples, some or all of the example methods of FIGS. 4, 5, 6 and 7 are embodied in coded instructions stored on a tangible machine accessible or readable medium such as a flash memory, a ROM and/or random-access memory RAM associated with a processor. Alternatively, some or all of the example methods of FIGS. 4, 5, 6, and 7 may be implemented using any combination(s) of application specific integrated circuit(s) (ASIC(s)), programmable logic device(s) (PLD(s)), field programmable logic device(s) (FPLD(s)), discrete logic, hardware, firmware, etc. Also, one or more of the operations depicted in FIGS. 4, 5, 6, and 7 may be implemented manually or as any combination of any of the foregoing techniques, for example, any combination of firmware, software, discrete logic and/or hardware. Further, although the example methods are described in reference to the flowcharts illustrated in FIGS. 4, 5, 6, and 7, many other methods of implementing the example methods may be employed. For example, the order of execution of the blocks may be changed, and/or some of the blocks described may be changed, eliminated, sub-divided, or combined. Additionally any or all of the example methods of FIGS. 4, 5, 6, and 7 may be carried out sequentially and/or carried out in parallel by, for example, separate processing threads, processors, devices, discrete logic, circuits, etc.

Figure 4:
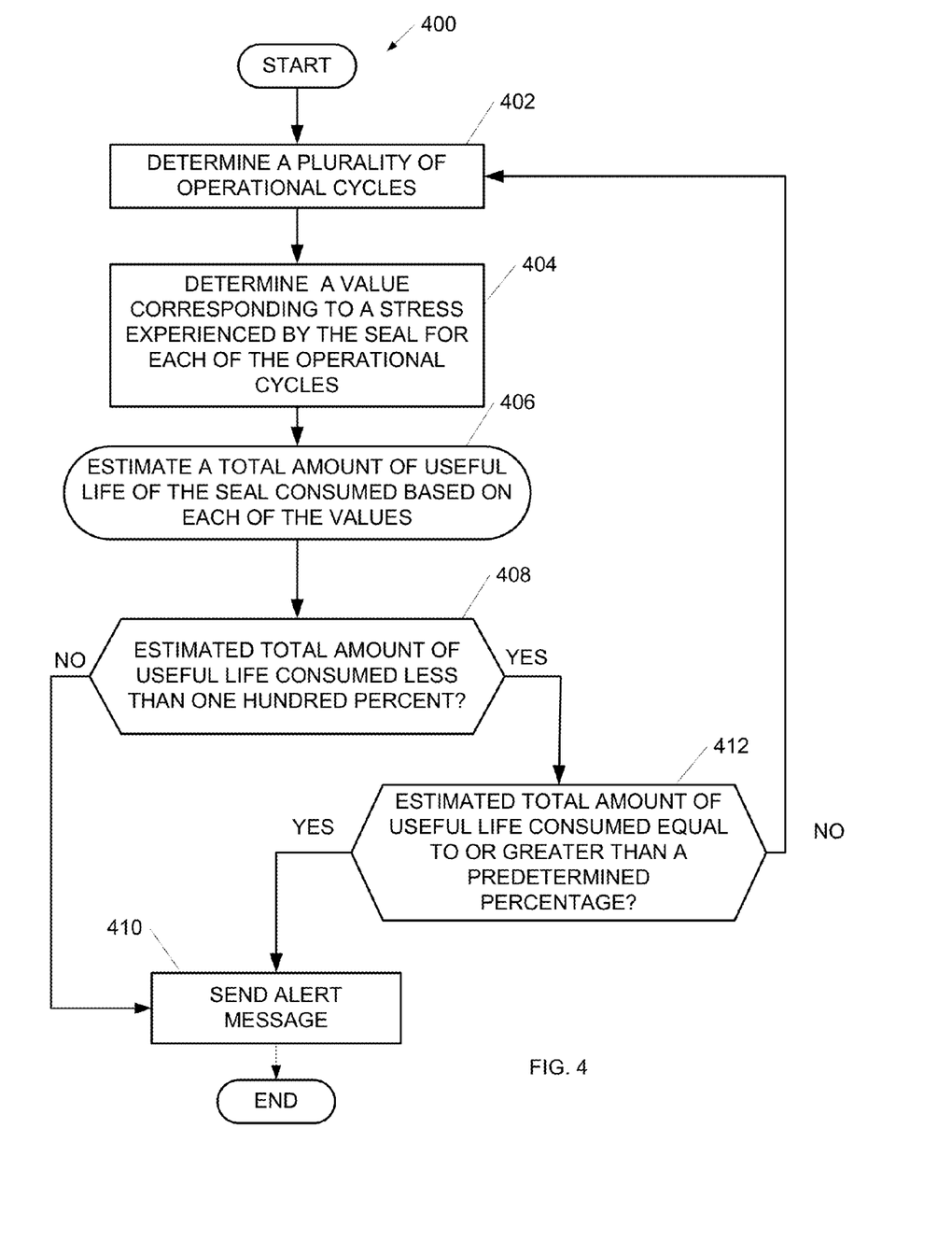
FIG. 4 is a flow chart representative of an example method disclosed herein.

With reference to FIGS. 1-3, the example method or process 400 of FIG. 4 begins by determining a plurality of operational cycles (block 402). In some examples, an operational cycle is movement of the stem 202 from a first position to a second position in one direction. During operation, the stem 202 moves a variety of distances while performing the plurality of operational cycles. The DVP 206 determines one of the operational cycles by determining movement of the stem 202 from the first to the second position in the one direction. At block 404, a value corresponding to a stress experienced by the seal 208 for each of the operational cycles is determined. In some examples, the value corresponding to the stress experienced by the seal 208 for each of the operational cycles is a distance traveled by the stem 202 during each of the operational cycles. For example, DVP 206 determines a position of the stem 202 at the first position, a position of the stem 202 at the second position, and then determines a distance between the first position and the second position.

In other examples, the value corresponding to the stress experienced by the seal 208 for each the operational cycles is a position of the stem 202 during each of the operational cycles farthest from the position of the stem 202 where the seal 208 experiences about zero stress. Based on each of the values for each of the operational cycles, the total amount of useful life of the seal 208 consumed is estimated (block 406). In some examples, the estimated total amount of useful life consumed is a fraction and/or a percentage.

At block 408, whether the estimated total amount of useful life consumed is less than one hundred percent is determined. If the estimated total amount of useful life consumed is one hundred percent or greater, an alert message is sent (block 410). For example, the DVP 206 and/or the controller 104 generates and sends the alert message to the workstation 108, which displays the alert message via the interface 110. If the estimated total amount of useful life consumed is less than one hundred percent, whether the total amount of useful life consumed is equal to or greater than a predetermined percentage is determined (block 412). If the total amount of useful life consumed is equal to or greater than the predetermined percentage, an alert message is sent (block 410). For example, the DVP 206 and/or the controller 104 may be set to generate and send the alert message to the workstation 108 when the estimated total amount of useful life consumed is eighty percent. If the estimated total amount of useful life consumed is less than one hundred percent and less than the predetermined percentage, then the example method 400 returns to block 402.

Figure 5:
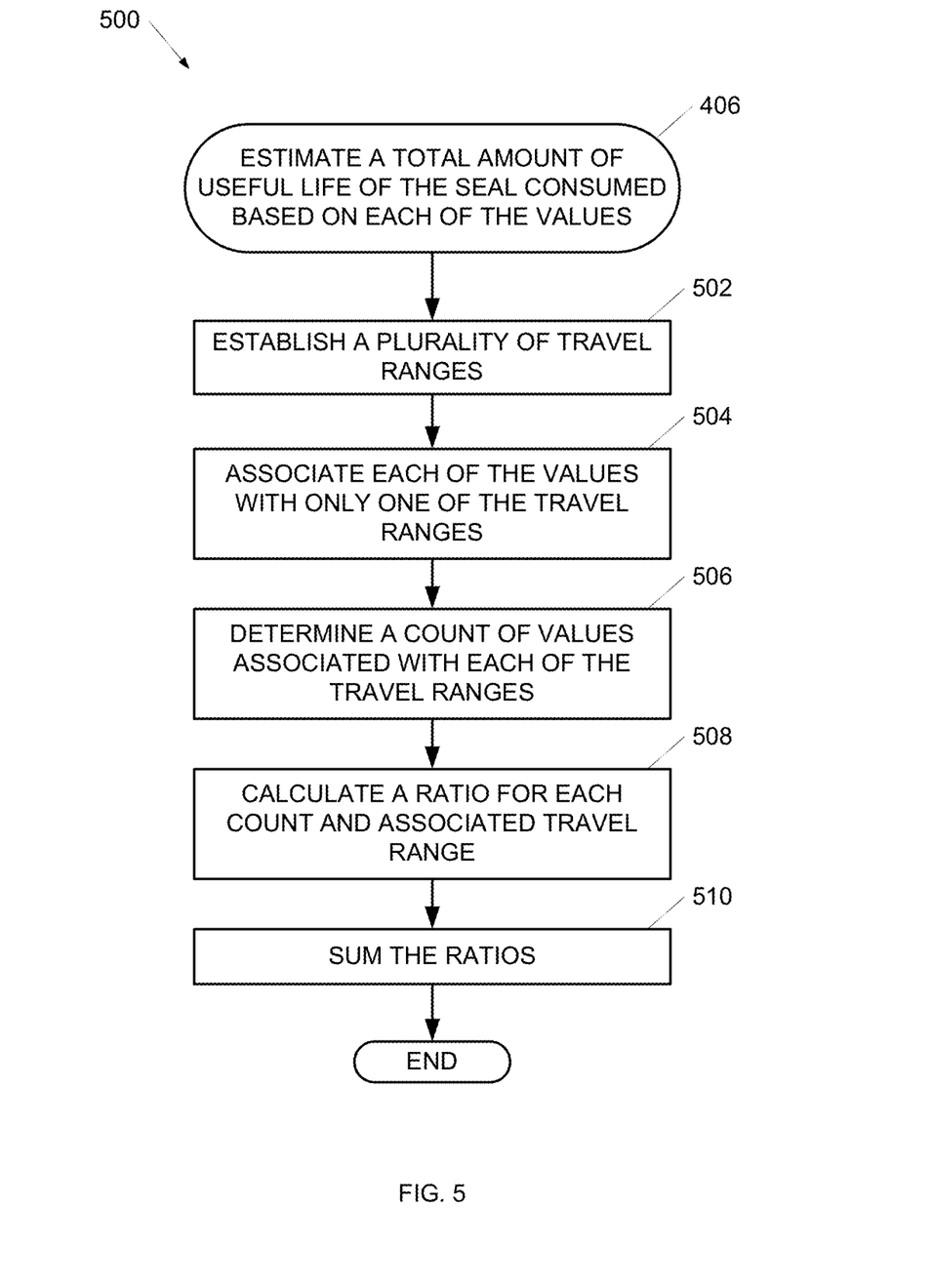
FIG. 5 is a flow chart representative of another example method disclosed herein.

FIG. 5 is a flowchart representative of an example process or method 500 of estimating the total amount of useful life of the seal 208 consumed based on each of the values (block 406). At block 502, a plurality of travel ranges is established. Each travel range corresponds to different values corresponding to stresses experienced by the seal. For example, one travel range may be 0 inches to 0.21 inches, and another travel range may be 0.22 inches to 0.28 inches. At block 504, each of the values is associated with only one of the travel ranges. For example, if the DVP 206 determines the value corresponding to the stress experienced by the seal 208 is 0.20 inches, then the value of 0.20 inches is associated with the travel range of 0 inches to 0.21 inches. In some examples, the values are determined by determining a distance traveled by the stem 202 during each of the operational cycles. In other examples, the values are determined by determining a position of the stem 202 during each of the operational cycles farthest from a position of the stem 202 where the seal 208 experiences about zero stress (e.g., a fully closed position). At block 506, a count of values associated with each of the travel ranges is determined. For example, if the DVP 206 associates the value of 0.20 inches with the travel range of 0 inches to 0.21 inches, the DVP 206 determines that a count of values associated with the travel range of 0 inches to 0.21 inches is increased by one.

At block 508, a ratio for each count and associated travel range is calculated. In some examples, the ratios include dividing each of the counts by a predetermined estimated cycle life value corresponding to the travel range associated with the count. The predetermined estimated cycle life values are determined by testing a plurality of other process control devices similar or identical to the process control device 200 of the example process control system 100. For example, a similar or identical process control device may be tested with a stem and bellows seal having a travel distance of 0.21 inches to or from a position where the seal experiences about zero stress per operational cycle (FIG. 3). The bellows seal of the similar or identical process control device fails after 8,000,000 operational cycles. Thus, the predetermined estimated cycle life value is 8,000,000 and corresponds to the travel range of 0 inches to 0.21 inches. During operation, if the DVP 206 determines a count of 3,000,000 values associated with the travel range 0 inches to 0.21 inches for the process control device 200 of the example process control system 100, the ratio equals $$\frac{3,000,000}{8,000,000} \text{ or } \frac{3}{8}.$$

At block 510, the ratios are summed to determine a value indicative of the total amount of useful life of the seal 208 consumed (e.g., $$\frac{9}{10},$$

90%, etc.).

In some examples, the estimated cycle life values are based at least in part on a process condition associated with the process control device 200 such as a temperature and/or a pressure. For example, the similar or identical process control devices may be tested at a pressure and/or temperature substantially equal to a pressure and/or temperature that the process control device 200 of the example process control system 100 is to be subjected to during operation.

Figure 6:
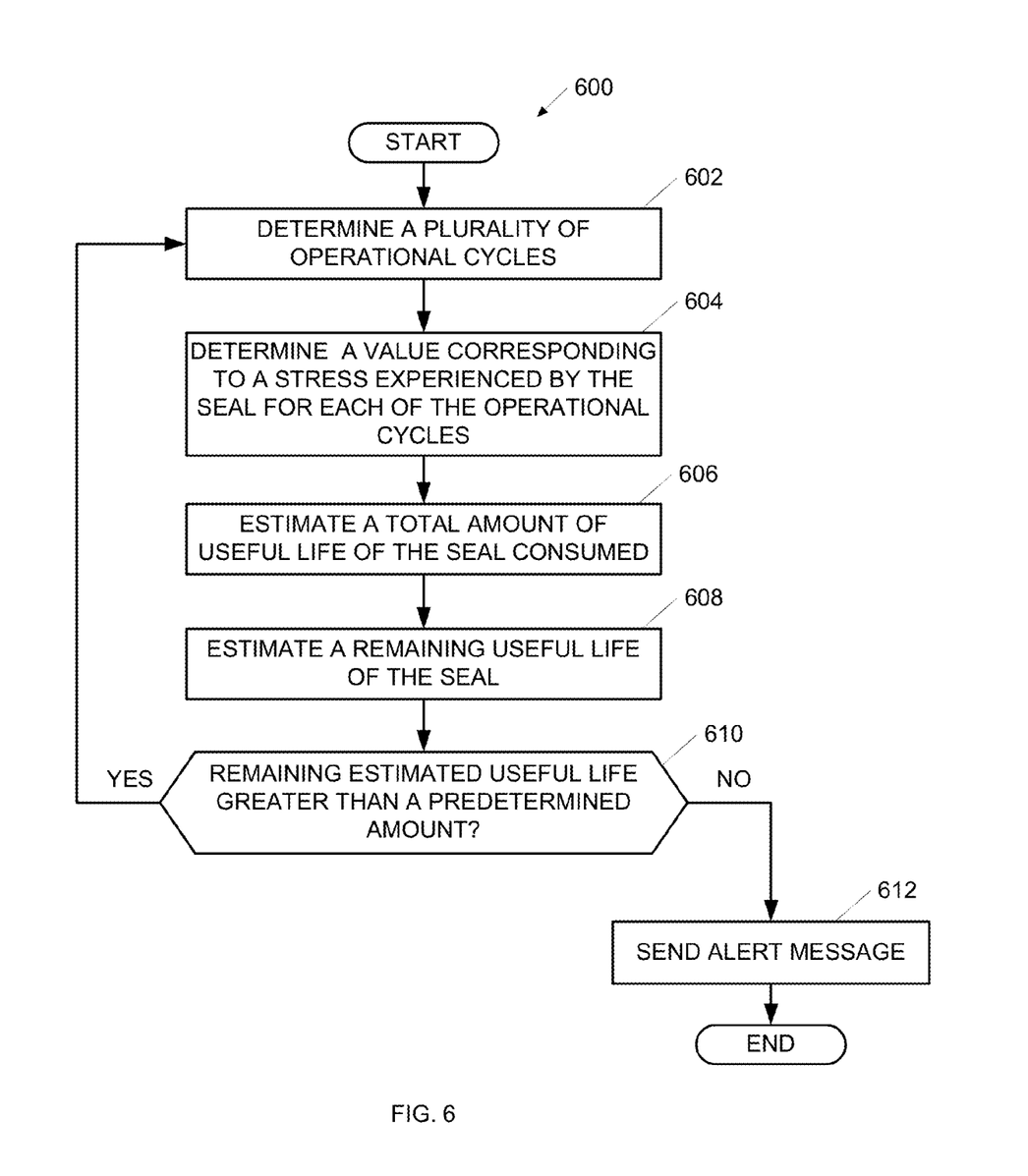
FIG. 6 is a flow chart representative of another example method disclosed herein.

FIG. 6 is a flowchart representative of an example process or method 600 of estimating a remaining useful life of the seal 208. The example process or method 600 begins by determining a plurality of operational cycles of the stem 202 of the process control device 200 (block 602). At block 604, a value corresponding to a stress experienced by the seal 208 for each of the operational cycles is determined. At block 606, based on each of the values, a total amount of useful life of the seal 208 consumed is estimated. A remaining useful life of the seal 208 is then estimated based on the estimated total amount of useful life of the seal 208 consumed (block 608).

For example, if the estimated total amount of useful life of the seal 208 consumed is 90 percent, the remaining useful life of the seal 208 is 10%. In some examples, estimating the remaining useful life of the seal 208 includes determining a frequency of the operational cycles and calculating the remaining useful life of the seal 208 based on the total amount of useful life of the seal 208 consumed and the frequency of operational cycles. For example, if the DVP 206 determines the frequency of the operational cycles is 100,000 per week and 90% of the useful life of the seal 208 is consumed after 9 weeks, the remaining useful life of the seal 208 is 100,000 operational cycles or one week at the determined frequency. In some examples, the remaining useful life of the seal 208 has units of hours, days, weeks, months, and/or any other suitable unit (e.g., 7 days).

At block 610, whether the estimated remaining useful life is greater than a predetermined amount is determined. If the estimated remaining useful life is greater than the predetermined amount, the example method 600 returns to block 602. If the estimated remaining useful life is not greater than the predetermined amount, then an alert message is sent (block 612). For example, if the predetermined amount equals the estimated remaining useful life, an alert message is sent by the DVP 206 and/or the controller 104 to the workstation 108.

Figure 7:
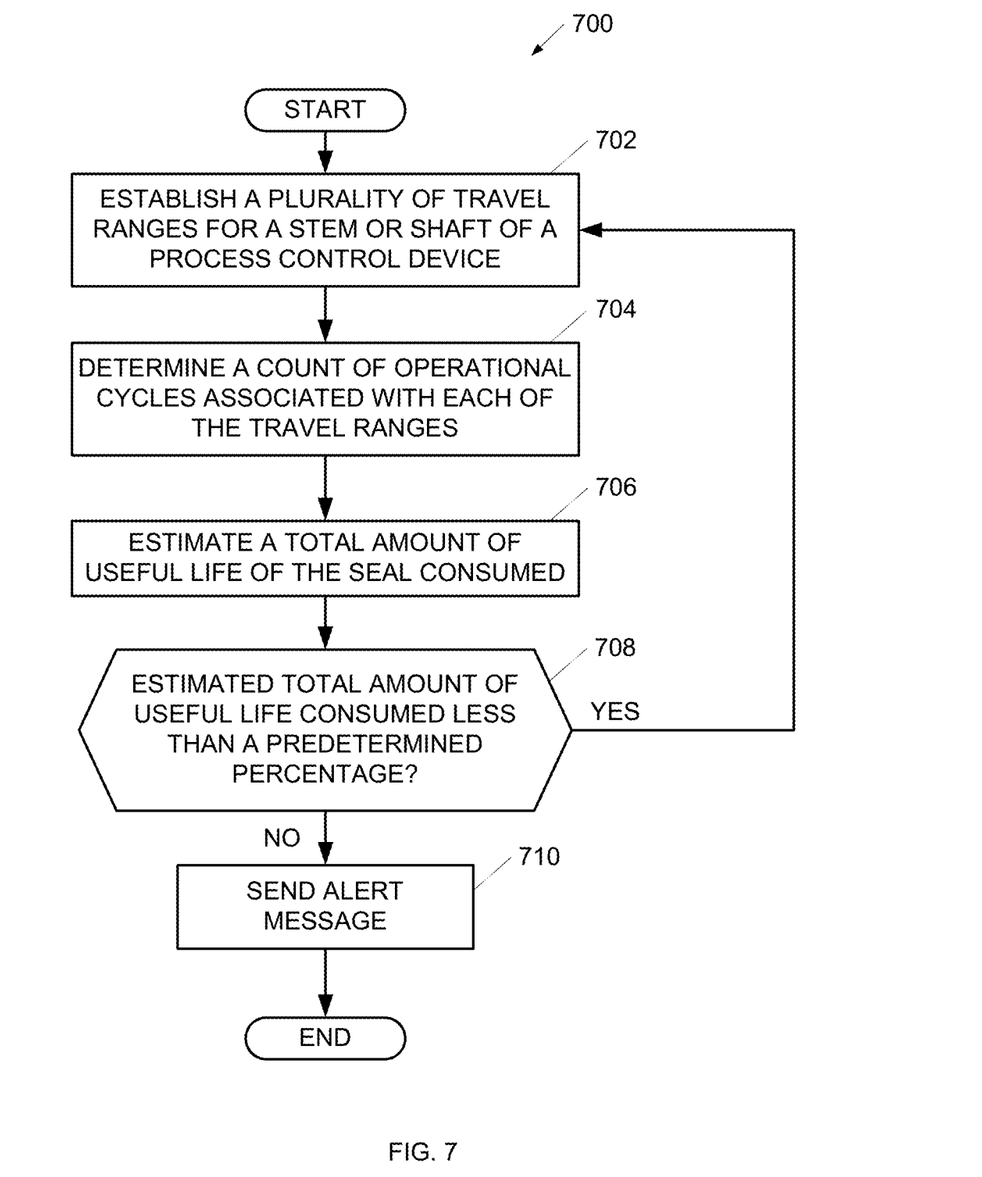
FIG. 7 is a flow chart representative of another example method disclosed herein.

FIG. 7 is a flowchart representative of another example process or method 700 disclosed herein. The example process or method 700 begins by establishing a plurality of travel ranges of the stem 202 of the process control device 200 (block 702). Each of the travel ranges corresponds to different values corresponding to stresses experienced by the seal 208 of the process control device 200 during an operational cycle. For example, the travel ranges may be 0 inches to 0.21 inches and 0.22 inches to 0.28 inches. At block 704, a count of operational cycles associated with each of the travel ranges is determined. For example, the DVP 206 determines an operational cycle and a value corresponding to the stress experienced by the seal 208 during the operational cycle. In some examples, the value is determined by determining a distance traveled by the stem 202 during the operational cycle. In other examples, the value is determined by determining a position of the stem 202 during the operational cycle farthest from a position of the stem 202 where the seal 208 experiences about zero stress (e.g., a fully closed position). If the value corresponding to the stress experienced by the seal 208 during the operational cycle is 0.15 inches, the operational cycle is associated with the travel range of 0 inches to 0.21 inches. Thus, the count of operational cycles associated with the travel range of 0 inches to 0.21 inches is increased by one. At block 706, based on the counts, the total amount of useful life of the seal 208 consumed is estimated. For example, a ratio for each count and associated travel range may be calculated. In some examples, calculating the ratios includes dividing each count by a predetermined estimated cycle life value (e.g., a predetermined estimated cycle life value illustrated in FIG. 3) according to the travel range associated with the count. The ratios are then summed to determine a value indicative of the total amount of useful life of the seal 208 consumed (e.g., 90%).

At block 708, whether the estimated total amount of useful life consumed is less than a predetermined percentage is determined. The predetermined percentage may be less than 100%. If the estimated total amount of useful life consumed is not less the predetermined percentage, then an alert message is sent (block 710). The alert message is sent prior to when the estimated total amount of useful life of the seal consumed is 100 percent. For example, the DVP 206 and/or the controller 104 may be set to generate and send an alert message to the workstation 108 when the estimated total amount of useful life is 90%. If the estimated total amount of useful life consumed is less than the predetermined percentage, than the example method 700 returns to block 702.

Although certain example methods and apparatus have been described herein, the scope of coverage of this patent is not limited thereto. On the contrary, this patent covers all methods, apparatus and articles of manufacture fairly falling within the scope of the appended claims either literally or under the doctrine of equivalents.

The Abstract at the end of this disclosure is provided to comply with 37 C.F.R. §1.72(b) to allow the reader to quickly ascertain the nature of the technical disclosure. It is submitted with the understanding that it will not be used to interpret or limit the scope or meaning of the claims.

What is claimed is:

1. A method of estimating useful life of a seal in a process control device, comprising:
   determining, via a processor, a plurality of operational cycles of a stem or shaft of the process control device;
   determining, via the processor, a value corresponding to a stress experienced between the seal and a plug for each of the operational cycles;
   estimating, via the processor, a total amount of useful life of the seal consumed based on each of the values; and
   estimating a remaining useful life of the seal based on the estimated total amount of useful life of the seal consumed, wherein estimating the remaining useful life of the seal comprises determining a frequency of the operational cycles and calculating the remaining useful life of the seal based on the total amount of the useful life of the seal consumed and the frequency of the operational cycles.

2. The method of claim 1, wherein the value corresponding to the stress experienced by the seal is corresponds to a distance traveled by the stem or shaft.

3. The method of claim 1, further comprising sending an alert message prior to when the estimated total amount of useful life of the seal consumed is one hundred percent.

4. The method of claim 1,
   further comprising associating each of the values with one of a plurality of travel ranges of the stem or shaft.

5. A method of estimating useful life of a seal in a process control device, comprising:
   determining, via a processor, a plurality of operational cycles of a stem or shaft of the process control device;
   determining, via the processor, a value corresponding to a stress experienced between the seal and a plug for each of the operational cycles;
   estimating, via the processor, a total amount of useful life of the seal consumed based on each of the values, wherein estimating the total amount of useful life of the seal consumed comprises:
      establishing a plurality of travel ranges of the stem or shaft, each travel range corresponding to different values corresponding to stresses experienced by the seal;
      associating each of the values with only one of the travel ranges;
      determining a count of values associated with each of the travel ranges;
      calculating a ratio for each count and the associated travel range; and
      summing the ratios to determine a value indicative of the total amount of useful life of the seal consumed.

6. The method of claim 5, wherein calculating the ratios comprises dividing each count by a predetermined estimated cycle life value corresponding to the travel range associated with the count.

7. The method of claim 6, further comprising determining the predetermined estimated cycle life values by testing a plurality of other process control devices similar or identical to the process control device.

8. The method of claim 5, wherein the values corresponding to the stresses experienced by the seal correspond to respective distances traveled by the stem or shaft.

9. A method of estimating useful life of a seal in a process control device, comprising:
determining, via a processor, a plurality of operational cycles of a stem or shaft of the process control device;
determining, via a processor, a value corresponding to a stress experienced between the seal and a plug for each of the operational cycles, wherein the value corresponding to the stress experienced by the seal is a position of the stem or shaft during each of the operational cycles farthest from a position of the stem or shaft where the seal experiences about zero stress; and
estimating, via a processor, a total amount of useful life of the seal consumed based on each of the values.

10. The method of claim 9, further comprising estimating a remaining useful life of the seal based on the estimated total amount of useful life of the seal consumed.

11. The method of claim 9, further comprising sending an alert message prior to when the estimated total amount of useful life of the seal consumed is one hundred percent.

12. A method of estimating useful life of a seal in a process control device, comprising:
establishing, via a processor, a plurality of travel ranges of a stem or shaft of the process control device, each travel range corresponding to different values corresponding to stresses experienced by the seal during an operational cycle;
determining, via the processor, a count of operational cycles associated with each of the travel ranges, wherein determining the count of operational cycles associated with each of the travel ranges comprises:
determining a plurality of operational cycles;
determining, via the processor, a value corresponding to a stress experienced between the seal and a plug of the process control device during each operational cycle; and
associating each of the values with only one of the travel ranges;
estimating, via the processor, a total amount of useful life of the seal consumed based on the counts, wherein estimating the total amount of useful life of the seal consumed comprises:
calculating a ratio for each count and associated travel range; and
summing the ratios to determine a value indicative of the total amount of useful life of the seal consumed.

13. The method of claim 12, wherein calculating the ratios comprises dividing each count by a predetermined estimated cycle life value corresponding to the travel range associated with the count.

14. The method of claim 12, further comprising estimating a remaining useful life of the seal based on the estimated total amount of useful life of the seal consumed.

15. The method of claim 14, wherein estimating the remaining useful life of the seal comprises determining a frequency of the operational cycles and calculating the remaining useful life of the seal based on the total amount of the useful life of the seal consumed and the frequency.

16. The method of claim 12, wherein the values corresponding to the stresses experienced by the seal are correspond to distances traveled by the stem or shaft.

17. A method of estimating useful life of a seal in a process control device, comprising:
establishing a plurality of travel ranges of a stem or shaft of the process control device, each travel range corresponding to different values corresponding to stresses experienced by the seal during an operational cycle, wherein the values corresponding to the stresses experienced by the seal correspond to positions of the stem or shaft during the operational cycles farthest from a position of the stem or shaft where the seal experiences about zero stress;
determining, via a processor, a count of operational cycles associated with each of the travel ranges; and
estimating, via the processor, a total amount of useful life of the seal consumed based on the counts.

18. The method of claim 17, wherein the values corresponding to the stresses experienced by the seal correspond to distances traveled by the stem or shaft.

19. An article of manufacture storing machine readable instructions which, when executed, cause a machine to:
determine a plurality of operational cycles of a stem or shaft of a process control device;
determine a value corresponding to a stress experienced between a seal and a plug of the process control device for each of the operational cycles;
estimate an amount of remaining useful life of the seal based on each of the values and an estimated total life;
establish a plurality of travel ranges of the stem or shaft, each travel range corresponding to different values corresponding to stresses experienced by the seal;
associate each of the values with only one of the travel ranges;
determine a count of values associated with each of the travel ranges;
calculate a ratio for each count and associated travel range; and
sum the ratios to determine a value indicative of a total amount of useful life of the seal consumed.

20. An article of manufacture storing machine readable instructions which, when executed, cause a machine to:
determine a plurality of operational cycles of a stem or shaft of a process control device;
determine a value corresponding to a stress experienced between a seal and a plug of the process control device for each of the operational cycles;
estimate an amount of remaining useful life of the seal based on each of the values and an estimated total life; and
calculate ratios by dividing each count by a predetermined estimated cycle life value corresponding to a travel range associated with the count.

* * * * *

UNITED STATES PATENT AND TRADEMARK OFFICE
CERTIFICATE OF CORRECTION

| | |
|---|---|
| PATENT NO. | : 9,062,771 B2 |
| APPLICATION NO. | : 13/371263 |
| DATED | : June 23, 2015 |
| INVENTOR(S) | : Shawn William Anderson |

It is certified that error appears in the above-identified patent and that said Letters Patent is hereby corrected as shown below:

In the Claims

In Column 8, line 29 (Claim 2):   Delete "is" before "corresponds"

In Column 10, line 4 (Claim 16):  Delete "are" before "correspond"

Signed and Sealed this
Third Day of May, 2016

Michelle K. Lee
*Director of the United States Patent and Trademark Office*